US011420036B2

(12) United States Patent
Shaked et al.

(10) Patent No.: US 11,420,036 B2
(45) Date of Patent: Aug. 23, 2022

(54) INFUSION SET

(71) Applicant: SteadyMed Ltd., Rehovot (IL)

(72) Inventors: Assaf Shaked, Tel Aviv (IL); Inna Dekel, Petah Tikva (IL); Jonathan Guillaume Jamin, Bury St. Edmunds (GB); Stephen Edward Augustyn, Milton Keynes (GB); Stewart Maddison Fox, Cambridge (GB); Peter Noymer, Los Gatos, CA (US)

(73) Assignee: SteadyMed Ltd., Rehovot (IL)

( * ) Notice: Subject to any disclaimer, the term of this patent is extended or adjusted under 35 U.S.C. 154(b) by 340 days.

(21) Appl. No.: 16/670,565

(22) Filed: Oct. 31, 2019

(65) Prior Publication Data

US 2020/0121909 A1    Apr. 23, 2020

Related U.S. Application Data (62) Division of application No. 14/737,204, filed on Jun. 11, 2015, now Pat. No. 10,463,847.

(51) Int. Cl.
*A61M 39/12* (2006.01)
*A61M 5/168* (2006.01)
(Continued)

(52) U.S. Cl.
CPC ............ *A61M 39/12* (2013.01); *A61M 5/145* (2013.01); *A61M 5/1413* (2013.01);
(Continued)

(58) Field of Classification Search
CPC .. A61M 39/12; A61M 39/08; A61M 39/1011; A61M 2039/1072;
(Continued)

(56) References Cited

U.S. PATENT DOCUMENTS 4,842,598 A    6/1989 Tran
4,843,598 A    6/1989 Medlin
(Continued)

FOREIGN PATENT DOCUMENTS

CA    2812877 A1    4/2012
DE    3621846 A1    1/1988
(Continued)

OTHER PUBLICATIONS

European Search report dated Mar. 4, 2016 in European Patent Application 11782228.8, all pages.
(Continued)

*Primary Examiner* — James D Ponton
(74) *Attorney, Agent, or Firm* — Foley & Lardner LLP (57) ABSTRACT

An exemplary infusion set includes a tubing, a first connector, and a second connector. The first connector connects a first terminus of the tubing to an exit port of an infusion pump, providing fluid communication between fluid being conveyed by the infusion pump and the tubing. The second connector connects a second terminus of the tubing to a delivery module, providing fluid communication between the tubing and the delivery module. Full engagement of the first connector and the exit port of the infusion pump actuates operation of the infusion pump.

8 Claims, 8 Drawing Sheets

(51) Int. Cl.
*A61M 5/14* (2006.01)
*A61M 5/145* (2006.01)
*A61M 39/08* (2006.01)
*A61M 39/10* (2006.01)
*A61M 5/36* (2006.01)
*A61M 5/50* (2006.01)

(52) U.S. Cl.
CPC .......... *A61M 5/16804* (2013.01); *A61M 5/36* (2013.01); *A61M 5/50* (2013.01); *A61M 39/08* (2013.01); *A61M 39/1011* (2013.01); *A61M 2039/1072* (2013.01)

(58) Field of Classification Search
CPC ................ A61M 5/1413; A61M 5/145; A61M 5/16804; A61M 5/36; A61M 5/50
See application file for complete search history.

(56) References Cited

U.S. PATENT DOCUMENTS

| | | |
|---|---|---|
| 4,886,514 A | 12/1989 | Maget |
| 5,062,834 A | 11/1991 | Gross et al. |
| 5,102,389 A | 4/1992 | Hauser |
| 5,108,852 A | 4/1992 | Tomantschger et al. |
| 5,109,850 A | 5/1992 | Blanco et al. |
| 5,134,046 A | 7/1992 | Chow et al. |
| 5,318,557 A | 6/1994 | Gross |
| 5,354,264 A | 10/1994 | Bae et al. |
| 5,436,372 A | 7/1995 | Yoshida et al. |
| 5,438,249 A | 8/1995 | Chang et al. |
| 5,505,706 A | 4/1996 | Maus et al. |
| 5,527,288 A | 6/1996 | Gross et al. |
| 5,563,004 A | 10/1996 | Buzzelli et al. |
| 5,643,207 A | 7/1997 | Rise |
| 5,677,083 A | 10/1997 | Tomiyama |
| 5,716,343 A * | 2/1998 | Kriesel ............... A61M 5/1409 604/132 |
| 5,814,020 A | 9/1998 | Gross |
| 5,827,233 A | 10/1998 | Futagawa et al. |
| 5,848,991 A | 12/1998 | Gross et al. |
| 5,938,640 A | 8/1999 | Maget et al. |
| 5,980,741 A | 11/1999 | Schnell et al. |
| 6,150,053 A | 11/2000 | Murata et al. |
| 6,186,982 B1 | 2/2001 | Gross et al. |
| 6,296,967 B1 | 10/2001 | Jacobs et al. |
| 6,312,409 B1 | 11/2001 | Gross |
| 6,322,532 B1 | 11/2001 | D'Sa et al. |
| 6,358,239 B1 | 3/2002 | Rake et al. |
| 6,377,848 B1 | 4/2002 | Garde et al. |
| 6,400,489 B1 | 6/2002 | Suzuki et al. |
| 6,465,125 B1 | 10/2002 | Takami et al. |
| 6,506,520 B1 | 1/2003 | Inoue et al. |
| 6,534,218 B1 | 3/2003 | Okada et al. |
| 6,537,249 B2 | 3/2003 | Kriesell et al. |
| 6,537,250 B1 | 3/2003 | Kriesel |
| 6,577,039 B2 | 6/2003 | Ishida et al. |
| 6,589,229 B1 | 7/2003 | Connelly et al. |
| 6,733,485 B1 | 5/2004 | Whitehurst et al. |
| 6,982,514 B1 | 1/2006 | Lu et al. |
| 7,242,134 B2 | 7/2007 | Wallace et al. |
| 7,364,568 B2 | 4/2008 | Angel et al. |
| 7,541,715 B2 | 6/2009 | Chiang et al. |
| 8,834,454 B2 | 9/2014 | Genosar et al. |
| 9,011,376 B2 | 4/2015 | Goldstein |
| 2002/0107480 A1 | 8/2002 | Kriesel et al. |
| 2002/0156461 A1 | 10/2002 | Joshi |
| 2002/0169439 A1 | 11/2002 | Flaherty |
| 2003/0014014 A1 | 1/2003 | Nitzan |
| 2003/0168120 A1 | 9/2003 | Brehm et al. |
| 2004/0039373 A1 | 2/2004 | Harding et al. |
| 2004/0059282 A1 | 3/2004 | Flock et al. |
| 2004/0068224 A1 | 4/2004 | Couvillon et al. |
| 2004/0115068 A1 | 6/2004 | Hansen et al. |
| 2004/0115523 A1 | 6/2004 | Hommura et al. |
| 2004/0115530 A1 | 6/2004 | Maeda et al. |
| 2004/0138612 A1 | 7/2004 | Shermer et al. |
| 2005/0096587 A1 | 5/2005 | Santini et al. |
| 2006/0052768 A1 | 3/2006 | Joshi et al. |
| 2006/0069344 A1 | 3/2006 | Southam et al. |
| 2006/0102455 A1 | 5/2006 | Chiang et al. |
| 2006/0106346 A1 | 5/2006 | Sullivan et al. |
| 2006/0184119 A1 | 8/2006 | Remde et al. |
| 2006/0200073 A1 | 9/2006 | Radmer et al. |
| 2007/0161978 A1 * | 7/2007 | Fedenia ............. A61B 18/1402 606/34 |
| 2007/0255237 A1 * | 11/2007 | Lobl ................. A61M 5/14276 604/288.01 |
| 2008/0188779 A1 | 8/2008 | Vellero |
| 2008/0265191 A1 | 10/2008 | Walborn |
| 2008/0281270 A1 | 11/2008 | Cross et al. |
| 2009/0069746 A1 | 3/2009 | Miller et al. |
| 2009/0093772 A1 | 4/2009 | Genosar et al. |
| 2009/0312706 A1 | 12/2009 | Shantha et al. |
| 2010/0001516 A1 * | 1/2010 | Pisula, Jr. ............. A61M 39/10 285/311 |
| 2010/0022992 A1 | 1/2010 | Genosar et al. |
| 2010/0056874 A1 | 3/2010 | Dijksman et al. |
| 2010/0130931 A1 | 5/2010 | Yodfat et al. |
| 2010/0152658 A1 | 6/2010 | Hanson et al. |
| 2010/0266638 A1 | 10/2010 | Turkel et al. |
| 2010/0274221 A1 | 10/2010 | Sigg et al. |
| 2011/0098652 A1 | 4/2011 | Haster et al. |
| 2011/0160655 A1 | 6/2011 | Hanson et al. |
| 2011/0208123 A1 * | 8/2011 | Gray ................... H01M 50/213 604/151 |
| 2011/0306929 A1 | 12/2011 | Levesque et al. |
| 2012/0041338 A1 | 2/2012 | Chickering, III |
| 2012/0042517 A1 | 2/2012 | Tronnes et al. |
| 2012/0238849 A1 | 9/2012 | Holtzclaw et al. |
| 2014/0107579 A1 | 4/2014 | Lanigan et al. |
| 2014/0148761 A1 | 5/2014 | Rotem et al. |
| 2014/0163339 A1 | 6/2014 | Goldstein et al. |
| 2014/0171867 A1 * | 6/2014 | Walsh ............... A61M 5/14244 604/111 |
| 2015/0017493 A1 | 1/2015 | Genosar et al. |
| 2015/0038907 A1 | 2/2015 | Rotem |
| 2015/0045718 A1 | 2/2015 | Shlomo |
| 2015/0190588 A1 * | 7/2015 | Hanson ................. A61M 5/36 604/123 |
| 2015/0265828 A1 * | 9/2015 | Colman ................ F16L 21/00 604/535 |
| 2015/0306365 A1 | 10/2015 | Besko |
| 2017/0304532 A1 | 10/2017 | Rotem |
| 2018/0035935 A1 | 2/2018 | Goldstein et al. |

FOREIGN PATENT DOCUMENTS

| | | | |
|---|---|---|---|
| DE | 19809483 | A1 | 9/1999 |
| EP | 0676214 | A1 | 10/1995 |
| EP | 1912690 | A1 | 4/2008 |
| EP | 2621558 | A1 | 8/2013 |
| EP | 2825225 | A1 | 1/2015 |
| EP | 2827923 | A1 | 1/2015 |
| GB | 2221394 | A | 2/1990 |
| IL | 169807 | | 2/2006 |
| JP | 02-131376 | A | 5/1990 |
| JP | 04-127885 | A | 4/1992 |
| WO | 97/010012 | A1 | 3/1997 |
| WO | 2001/021234 | A1 | 3/2001 |
| WO | 01/51108 | A1 | 7/2001 |
| WO | 2004/067066 | A1 | 2/2003 |
| WO | 2004/006982 | A2 | 1/2004 |
| WO | 2005/124918 | A2 | 12/2005 |
| WO | 2007/010522 | A1 | 1/2007 |
| WO | 2007/129317 | A1 | 11/2007 |
| WO | 2008/062335 | A1 | 5/2008 |
| WO | 2008/122983 | A1 | 10/2008 |
| WO | 2011/075100 | A1 | 6/2011 |
| WO | 2012/042517 | A1 | 4/2012 |

(56) References Cited

FOREIGN PATENT DOCUMENTS

WO  2013/136327 A1  9/2013
WO  2013/140395 A1  9/2013

OTHER PUBLICATIONS

European Search Report for EP 15171662.8 dated Apr. 13, 2016, 10 pages.
Lee et al., "Battery Dimensional Changes Occuring During Charge/Discharge Cycles—Thin Rectangular Lithium Ion and Polymer Cells," Journal of Power Sources, 119-121: 833-837 (2003).
International Search Report and Written Opinion for PCT/IL2007/000548 dated Sep. 18, 2007, all pages.
International Search Report and Written Opinion for PCT/IL2006/000769 dated Oct. 30, 2006, all pages.
International Preliminary Report on Patentability for PCT/IL2006/000769 dated Jan. 22, 2008, all pages.
International Search Report and Written Opinion for PCT/IL2013/050223 dated Jun. 24, 2013, all pages.
International Preliminary Report on Patentability for PCT/IL2013/050223 dated Sep. 16, 2014, all pages.
International Search Report and Written Opinion for PCT/IL2013/050240 dated Jul. 2, 2013, all pages.
International Preliminary Report on Patentability for PCT/IL2013/050240 dated Sep. 23, 2014, all pages.
International Preliminary Report on Patentability for PCT/IL2007/000548 dated Nov. 11, 2008, all pages.
International Search Report and Written Opinion for PCT/IL2011/000757 dated Jan. 11, 2012, all pages.
International Preliminary Report on Patentability for PCT/IL2011/000757 dated Apr. 2, 2013, all pages.
Notice of opposition to a European patent for Patent No. EP 2015806 dated Jun. 1, 2010, 16 pages.

* cited by examiner

INFUSION SET

CROSS-REFERENCE TO RELATED APPLICATIONS

This application is a divisional of U.S. patent application Ser. No. 14/737,204, filed Jun. 11, 2015, and entitled "INFUSION SET," (issued as U.S. Pat. No. 10,463,847 on Nov. 5, 2019) the entire contents of which are herein incorporated by reference.

BACKGROUND OF THE INVENTION

Infusion treatment is a common medical practice for delivering a medicament to a patient. Infusion treatment typically entails delivering a fluid infusate to a patient with an infusion device, most commonly an infusion pump. The infusate is typically provided by an infusion set having an infusate source, an infusate tube extending from the infusate source and a slide clamp adapted to receive the infusate tube. The slide clamp, which assists with infusate flow regulation, and the infusate tube when connected to the infusion pump place the infusate in fluid communication with the infusion pump.

Delivery of the infusate to the patient typically involves the physical and/or mechanical manipulation of the infusate tube by the infusion pump. Conventional infusion pumps customarily include parameters that may be adjusted in order to adapt to specific infusion set administration protocols delivery requirements. The parameters may include settings to accommodate the composition of the infusate, the physical and/or material properties of the infusate tube and the flow rate for effective infusate delivery, for example. The parameters may also include settings to accommodate the use of a special set compatible with a specific infusate, or to accommodate the use of a special set including a specific set component such as a particular valve or sensor.

A need therefore exists to reduce the risk of inaccurate and dangerous delivery of an infusate to a patient. A need further exists for an automated infusion set that is custom designed for the infusion delivery system thereby ensuring the proper delivery of the infusate by the infusion pump. A need further exists for a convenient, automated infusion system that permits patient self-administration of infusion treatment either at a health care facility or in the home.

Infusion sets are typically used in both intravenous and subcutaneous medication administration protocols.

Subcutaneous injection is a standard method for the delivery of medication into a patient's body. To facilitate frequent or continuous subcutaneous injection of medication, subcutaneous injection ports are often used. Such injection ports extend through the skin and may remain in place for several days. Currently, a major application of such injection ports is to provide continuous delivery of medication, such as insulin, from portable pumps carried with the patient. When used with a portable pump, the injection port is typically connected to the pump via a fluid line. Another application of subcutaneous injection ports is to permit multiple injections of medication into a patient without the need to re-puncture the patient's skin. In this application, medication is injected from a standard medical implement, such as a syringe, through a soft elastomer septum into the injection port which delivers the medication subcutaneously.

There remains a need for an improved infusion set that is less bulky, less susceptible to contamination, less susceptible to flow fluctuation and siphoning effects, more comfortable to a user, and easier to use.

BRIEF SUMMARY OF THE INVENTION

This invention provides an infusion set suitable for delivery of a medication via both subcutaneous (SC) and intravenous (IV) administration routes.

This invention also provides an infusion set comprising elements, such as a proximal connector connecting the infusion set to an infusion pump via a water-tight sealed mechanism, tubing, through which a medication is delivered during infusion, and a distal adaptor connecting the tubing to a subcutaneously placed cannula or intravenous line, further comprising a modified proximal connector, which actuates operation of the infusion pump upon insertion therewithin. In some aspects, the proximal connector may comprise an element that actuates a switch, which in turn actuates operation of the infusion pump.

In some aspects, any means of actuation of the infusion pump is envisioned, for example, whereby a physical switch or optical switch or sensor relay facilitates actuation of the pump operationally connected thereto.

It will be appreciated that any means of pump actuation is envisioned, and that one aspect and embodied advantage of the devices of this invention provide for connection of the infusion set connector to the infusion pump, which step regulates pump activation, i.e. connecting the infusion set activates pump activity.

In some aspects, the infusion set proximal connector may be positioned such that it enables opening a drug path to allow fluid flow through said infusion set, while being located within a sealed drug delivery device so that only the fluid path opening and closure is impacted.

In some aspects, for example, the proximal connector may be so positioned as to occupy a given port or placement within a device, which facilitates opening of a fluid path (for example one that it formerly blocked), which does not impact the sealed device casing.

In some aspects, the tubing in the embodied infusion sets comprises at least a section having a narrow bore diameter, for example, of about 20-60 µm, or in some embodiments, of appropriate diameter to promote the restriction effect as described.

In some embodiments, the length of tubing will vary, such that the tubing will comprise a narrow bore diameter over its entire length, or in some embodiments, over a desired minimal tubing length to promote the restriction effect.

In some embodiments, envisioned overall tubing lengths will be from about 1 mm to about 5 cm, or in some embodiments, from about 10 micrometers to about 30 cm, or any range therein, which is useful in application as an infusion set as appropriate for the applications as described herein.

It will be appreciated by the skilled artisan that the tubing bore diameter and length will be adjusted to promote the restriction effect as described herein, representing the arrival at an ideal compromise between a bore diameter sufficiently narrow to prevent significant fluid siphoning and sufficiently wide to prevent occlusion.

For example, and in some embodiments, the infusion pump will be connected to a tubing section with a narrower diameter than that of the tubing located proximally to the subcutaneously placed cannula or intravenous line, providing for pressurization in the drug reservoir within the infusion pump, such that when an actuator located within an infusion pump in a device making use of the infusion sets of this invention moves at a defined speed for drug release therewithin, increased pressure will be required to expel the drug for the established flow rate, which in turn, in some embodiments, aids in the maintenance of the drug reservoir shape and delivery accuracy during operation.

In some aspects, the tubing in the embodied infusion sets has a narrow bore diameter over its entire length. According to this aspect, and in some embodiments, the narrow bore tubing diameter will range from about 40 to about 150 μm or in some embodiments, from about 60 to about 100 μm, or in some embodiments, from about 70 to about 95 μm, or in some embodiments, from about 60 to about 80 μm, In some embodiments, the narrower bore provides for flow restriction, which, in some aspects, damps out flow rate fluctuations and reduces siphoning effects.

In another aspect, the embodied infusion sets are tolerant of the presence of air bubbles in the delivery system, while preventing occlusion of the tubing and downstream delivery elements by closely matching the normal operating pressure and the bubble release pressure. For example, and in some embodiments, the increased pressurization of the drug reservoir container as a consequence of the reduced diameter of the tubing or in some embodiments, at least of the tubing located proximally thereto in the infusion sets of this invention result in greater driving pressure to release any air bubbles introduced into the tubing, for example, via surface tension effects. In some embodiments, the infusion sets of this invention and application of same promote the presence of some backpressure in the delivery device, yet an appropriate compromise is achieved in the infusion set design of this invention to promote some restriction yet not suffer the limitation of frequent or inappropriate blockage in the infusion set, for example.

In some aspects, since the tubing diameter required for same is quite low, and comparable to the diameter needed for drug expulsion, the same limits the back pressure incidence or magnitude, and prevents occlusion in the pump often characterizing other similar systems when an air bubble is inadvertently introduced.

In some aspects the infusion sets of this invention are so constructed to provide an inner bore diameter sufficiently small and accommodating for example, a drug delivery device so constructed such that occlusion of the infusion set is prevented, or in some embodiments, such infusion set tubing length and bore diameter are so chosen to maximize egress of any accumulated air bubbles preventing occlusion of the device. In some aspects, the construction specifically includes extending the tubing to contain an extended region of restriction to accomplish same.

In some aspects, such narrow bore tubing may provide an added advantage in terms of the drug stability for drugs maintained in the drug reservoir, which in some embodiments is attributable to reduced evaporation of same.

In some aspects, the invention provides an infusion set capable of extreme accuracy, wherein back pressures can be adjusted and in some aspects, support different infusion flow rates and/or fluid viscosities.

In some aspects, the invention further promotes the ability to customize back pressure by adjusting the inner diameter and/or length of the tubing, or in some embodiments, by using appropriate flow restriction valves.

In some aspects, the invention provides an infusion set with a connector that has a means to automatically start the infusion pump and simultaneously lock same in place, in a controlled manner, only when fully connected.

In some aspects, the controlled infusion pump initiation is via use of mechanical actuation of a switch, or in some embodiments, via use of magnetic actuation of a switch.

Figure 3A:
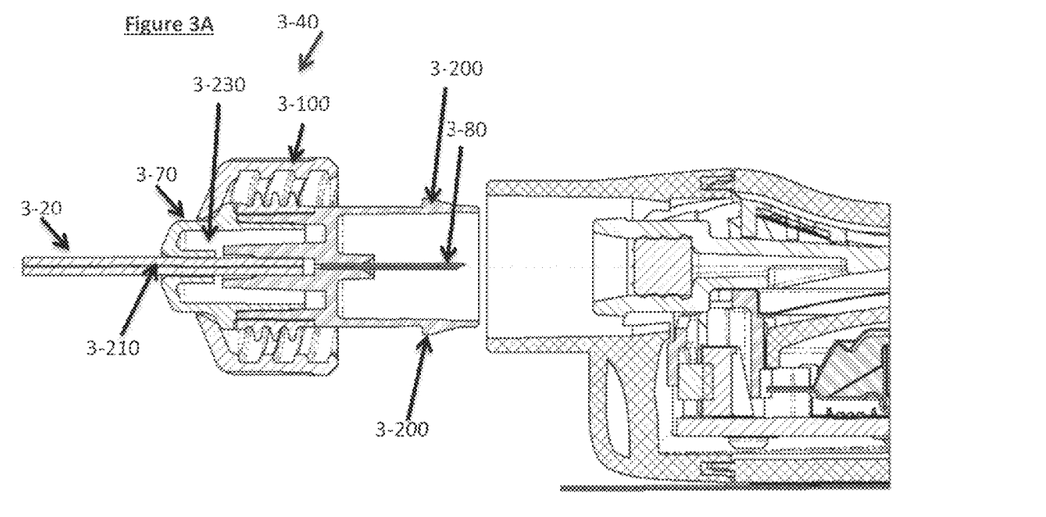
FIG. 3A-3C depicts a cross section of an embodied connector joining the tubing to an infusion pump and engagement of various elements during such joining.
Figure 3B:
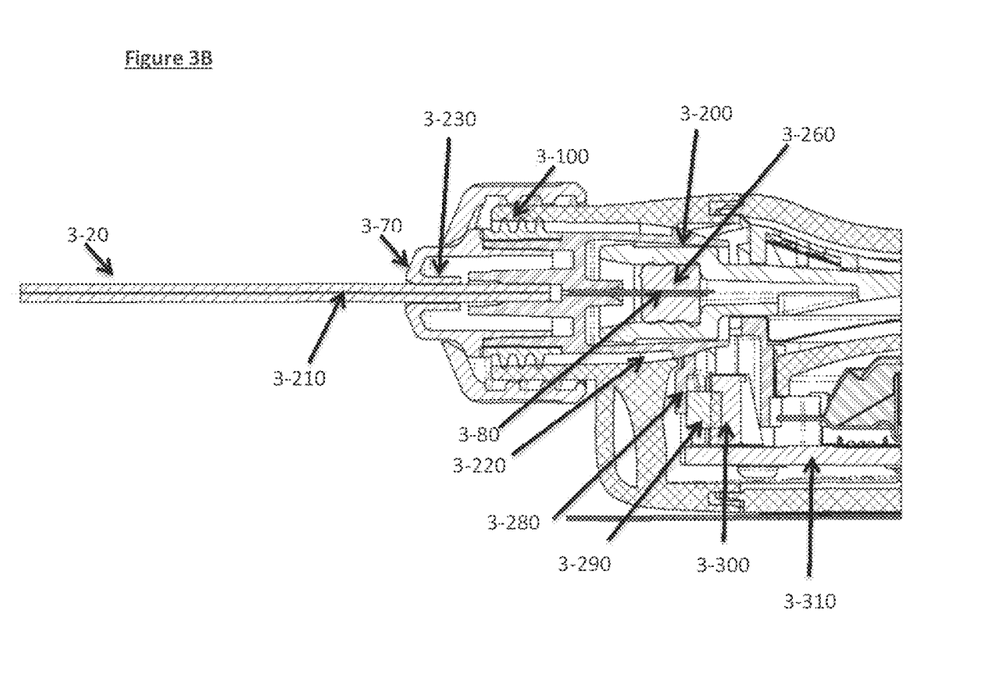
Figure 3C:
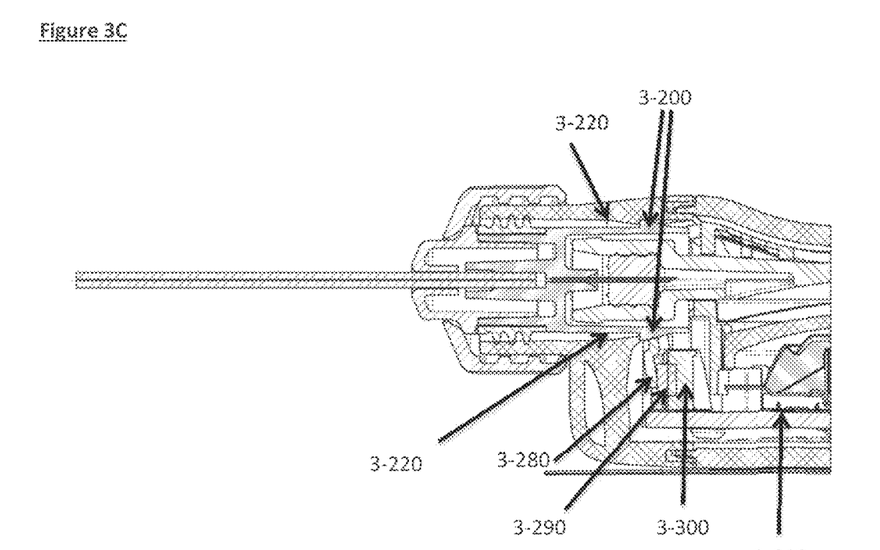

For example, and referring to FIGS. 3A-3C, once the connector is connected to the infusion pump, as embodied in this exemplified aspect, mechanical actuation may be via the movement of a cantilever 3-280, when an adapted region of the connector 3-200 fully engages an abutment 3-220 on the infusion pump. Further advancement of the adapted region 3-200 results in for example, lateral displacement of the cantilever, which in turn pushes a switch button 3-290, activating a switch 3-300, which results in downstream activation of the infusion pump, via, for example, the operationally connected PCB. Simultaneous to same, the septum 3-260 is pierced by the advancing needle 3-80, which promotes egress of the active contained agent within the infusion pump, concurrent with pump activation to allow for efficient delivery of the pump contents.

In some aspects, such controlled regulation may also include the switching off of the infusion pump when the connector is removed (i.e., the switch is disengaged when the activation element is removed).

In some embodiments, such controlled regulation may also allow for the continued pump engagement even if the connector is removed (i.e., the switch remains engaged when the activation element is removed).

In some embodiments, the infusion set comprises a means for piercing a septum or seal of the drug container in order to establish the fluid flow path while at the same time retaining water-tightness and activating the pump. While one embodied scheme of same is provided in FIGS. 3A-3C, the skilled artisan will appreciate that any number of arrangements for coordinated fluid path creation and pump activation are envisioned.

In some embodiments, the infusion set further comprises a means for creating back pressure, wherein the device is still tolerant to the presence of air bubbles introduced in the infusion line. In some embodiments, the back pressure created is within a range of 30-50 mbar, and as will be appreciated by the skilled artisan, in fact, such pressure range is influenced by the flow rate and drug viscosity and is adjusted accordingly.

In some aspects, the tubing length in the embodied infusion sets of this invention will be relatively short, which will facilitate convenient wearing of an on-body pump, or in some embodiments, will facilitate short priming durations for a pump with low volume flow rates. According to these aspects, the tube length may range, in some embodiments, from 5 cm (lower limit) to 100 cm.

In some aspects, the tubing in the embodied infusion sets of this invention will possess a narrow inner diameter, which, in some embodiments, will facilitate a short priming duration for a pump with low volume flow rates. According to these aspects, the tubing will have an inner diameter ranging from 0.08 mm and more and pump flow ranges may be from 20-300 μl/hr and scaled upward, as necessary, depending upon the infusion pump assembly in use with the infusion sets of this invention.

In some aspects, the tubing of the embodied infusion sets will comprise small bore tubing in order to reduce a siphoning effect, or in some embodiments, in order to prevent large particles being conveyed in the infusion line, which in some embodiments provides for an added safety feature.

In some aspects, the tubing of the embodied infusion sets will comprise small bore tubing in order to damp or smooth out any unintended bolus or any other overdosing scenario in using the embodied infusion sets and devices incorporating same.

BRIEF DESCRIPTION OF THE DRAWINGS

FIG. 2 depicts an embodied connector 2-40 as depicted in FIGS. 1A and 1B. Shown are the connector nut 2-50 containing a sealing element 2-100. The connector contains an internal needle 2-80 immobilized within a needle shroud 2-90. The seal retainer, 2-70, may hold the sealing element in place.

FIG. 3A shows the connector and pump elements prior to engagement of same. Shown are the connector nut 3-40. As the connector engages the infusion pump housing, a modified lateral element 3-200 on the connector makes contact with and advances over an abutment 3-220 on the infusion pump Case. Simultaneously the needle 3-80 pierces the septum 3-260, the connector becomes locked into the casing of the pump and the lateral extension 3-200 presses down on the cantilever 3-280, which causes the cantilever to laterally displace, thus engaging and moving a button on a proximal switch 3-290, which then promotes actuation of the infusion pump.

FIGS. 7D-1-A, 7D-1-B, 7D-1-C, 7D-1-D, 7D-1-E, 7E, 7F-1-A, 7F-1-B, 7F-1-C, 7F-1-D, 7F-1-E, and 7F-1-F, are photographs depicting the transit of an air bubble introduced in element 7-20, as it transits through the element 7-20 until its release therefrom, following the application of increased pressure.

DETAILED DESCRIPTION OF THE INVENTION

This invention provides an infusion set suitable for delivery of a medication via both subcutaneous (SC) and intravenous (IV) administration routes.

In one embodiment, the infusion sets of this invention comprise tubing, a first connector, which first connector connects a first terminus of said tubing to an exit port of an infusion pump, wherein a fluid being conveyed by said infusion pump is in fluid communication with said tubing; and a second connector which connects a second terminus of said tubing to a delivery module, providing fluid communication between said tubing and said delivery module; wherein full engagement of said first connector and said exit port of said infusion pump actuates operation of said infusion pump.

This invention also provides an infusion set comprising elements, such as a proximal connector connecting the infusion set to an infusion pump via a water-tight sealed mechanism, tubing, through which a medication is delivered during infusion, and a distal adaptor connecting the tubing to a subcutaneously placed cannula or intravenous line, further comprising a modified proximal connector, which actuates operation of the infusion pump upon insertion therewithin.

This invention also provides an infusion set comprising elements, such as a proximal connector connecting the infusion set to an infusion pump, whereby the tubing comprises at least a portion having a narrow bore diameter.

In some aspects, the infusion set proximal connector may be positioned such that it enables opening a drug path to allow fluid flow through said infusion set, while being located within a sealed drug delivery device so that only the fluid path opening and closure is impacted. In some aspects, for example, the proximal connector may be so positioned as to occupy a given port or placement within a device, which facilitates opening of a fluid path (for example one that it formerly blocked), which does not impact the sealed device casing.

In some aspects, the sealing may make use of a gasket located on the infusion set proximal connector, which is pressed against the casing of the device to prevent water leakage into the pump.

In some aspects, the element comprises a rubber gasket material being used in conjunction with a threaded fitting.

It is to be appreciated that various permutations of the device elements will allow for the drug path being open for infusion, while the pump itself is kept water tight.

In some aspects, when the proximal connector is pushed into the device in order to pierce the septum, it may also move a switch connected to the device electronics systems.

According to this aspect, and in one embodiment, once this mechanical switch is pressed it may in turn power up the device.

In some aspects, the element comprises the proximal connector having a nub or projection that fits a slot on the pump when the connector is attached, and when fully attached, the nub pushes a switch that starts the pump.

Figure 1A:
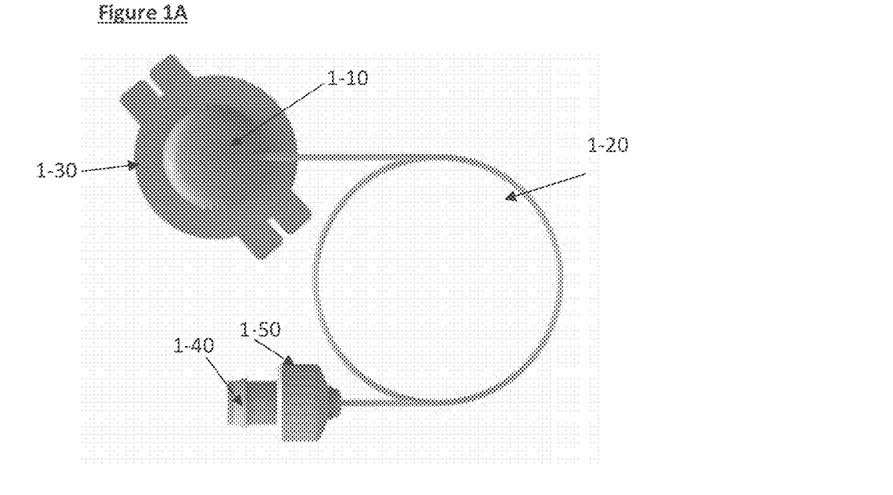
FIG. 1A depicts an embodied tubing set assembly for use in infusion sets for subcutaneous drug delivery. A cannula 1-30 connected to tubing 1-20 via the cannula connector 1-10 and further connected to a connector body 1-40 and connector nut 1-50 is shown.

FIG. 1A depicts an embodied tubing set assembly for use in infusion sets for subcutaneous drug delivery. A cannula 1-30 is connected to tubing 1-20 via the cannula connector 1-10. The tubing 1-20 is also connected to an infusion pump via the connector, by attachment of the connector body 1-40 to the pump and creating a tightly sealed fit with the use of the connector nut 1-50.

The tubing 1-20 will either comprise a narrow bore diameter along its entire length, or in some embodiments, a partial length of the tubing 1-20 will comprise a narrow bore diameter as herein described.

Figure 1B:
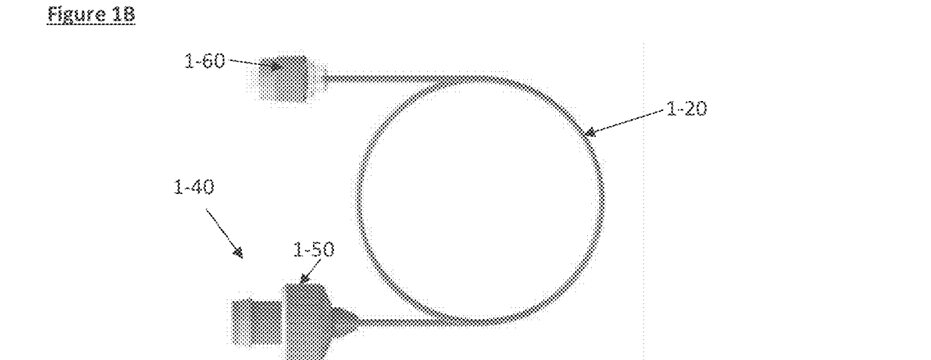
FIG. 1B depicts an embodied tubing set assembly for use in infusion sets for intravenous drug delivery. A catheter is connected to tubing 1-20 via the Luer connector 1-60 and the tubing 1-20 is also connected to the connector body 1-40 and connector nut 1-50.

FIG. 1B depicts an embodied tubing set assembly for use in infusion sets for intravenous drug delivery. A catheter is connected to tubing 1-20 via for example, a Luer connector 1-60. The tubing 1-20 is also connected to an infusion pump via the connector, by attachment of the connector 1-40 to the pump and creating a tightly sealed fit, for example, with the use of the connector nut 1-50.

Figure 2:
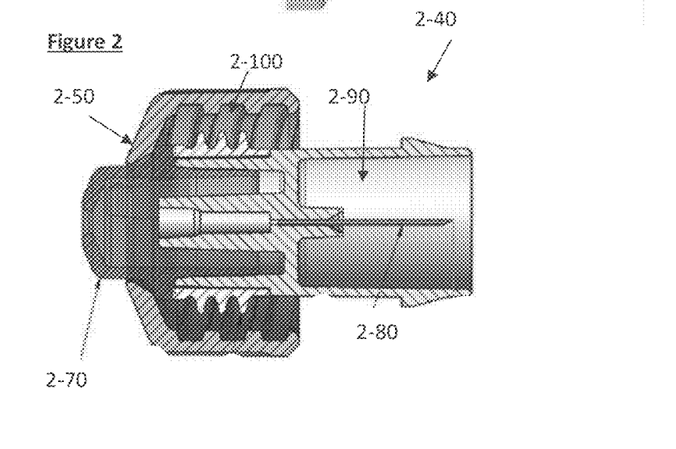

FIG. 2 depicts an embodied connector as depicted in FIGS. 1A and 1B. An infusion pump is connected to tubing 2-20 via the connector, by securing the connector nut 2-50 onto appropriately adapted infusion pump housing. The connector nut contains a sealing element 2-100, which facilitates a water-tight seal with the pump housing. The connector contains an internal needle 2-80 immobilized within a needle shroud 2-90. The needle 2-80 ultimately pierces a corresponding sealing element in the drug-containing reservoir assembly in the infusion pump, located in the pump housing.

The connector may further comprise a needle shroud 2-90, functioning to shield the needle from accidental stick injuries, as well as guiding and locking the connector to the pump casing. The seal retainer 3-70 may also keep the seal in place. Sealing may be maintained, in some embodiments, between the Case housing and connector via a water tight seal (3-100), e.g. using appropriate rubber structures, or other similar water tight sealing material.

FIG. 3 depicts a cross section of an embodied connector joining the tubing to an infusion pump. The connector nut contains a cut away to expose the connector body. Fine bore tubing 3-210 in the connector serves to facilitate conveying fluid exiting the pump and through the infusion set tubing. Seen also is the neck of the drug containing chamber 3-250, which is stoppered by the septum 3-260, preventing leakage of the container contents inadvertently. The Needle 3-80 is evident, as well, and its location within and piercing the septum 3-260.

FIGS. 3A, 3B and 3C depict various features involved in the engagement and ultimate locking of the connector in place and actuation of the infusion pump. As the connector engages the infusion pump housing, a cantilever 3-280 engages and moves a proximal switch 3-290, which then promotes actuation of the infusion pump.

Once the connector 3-40 is connected to the infusion pump, as embodied in this exemplified aspect, mechanical actuation may be via the movement of a cantilever 3-280, when an adapted region of the connector 3-200 fully engages an abutment 3-220 on the infusion pump.

Further advancement of the adapted region 3-200 results in for example, lateral displacement of the cantilever, which in turn pushes a switch button 3-290, activating a switch 3-300, which results in downstream activation of the infusion pump, via, for example, the operationally connected PCB 3-310. Simultaneous to same, the septum 3-260 is pierced by the advancing needle 3-80, which promotes egress of the active contained agent within the infusion pump, concurrent with pump activation to allow for efficient delivery of the pump contents.

It will be apparent to the skilled artisan that many other embodied permutations may be envisioned for the simultaneous creation of a fluid path and engagement of or actuation of the delivery pump to promote activation of the pump and fluid delivery from same upon full engagement of the connector. It will further be appreciated that the combination of such arrangement as well as the inclusion of tubing in the infusion set further comprising at least a partial length of same with a narrow bore diameter creates optimal fluid delivery, with least deleterious impact of occluding air bubbles, or least negative influence of undesirable siphoning effect.

In one embodiment, the infusion set comprises a tubing, which tubing comprises at least a first tubing length having a first inner diameter, which first tubing length is connected in a water-tight sealed manner to a second tubing length, which second tubing length has a second inner diameter which is larger than that of said first inner diameter; a first connector which connects a first terminus of said tubing to an exit port of an infusion pump, wherein a fluid being conveyed by said infusion pump is in fluid communication with said tubing; and a second connector which connects a second terminus of said tubing to a delivery module, providing fluid communication between said tubing and said delivery module; wherein said first connector and said second connector are connected to said tubing in a water-tight sealed manner.

In another embodiment, the infusion set comprises a tubing, which tubing comprises narrow bore diameter tubing having an inner diameter of less than 150 microns; a first connector which connects a first terminus of said tubing to an exit port of an infusion pump, wherein a fluid being conveyed by said infusion pump is in fluid communication with said tubing; and a second connector which connects a second terminus of said tubing to a delivery module, providing fluid communication between said tubing and said delivery module.

In some embodiments, according to this aspect, the tubing will have a narrow bore diameter from 40 to 150 µm. In some embodiments, according to this aspect, the tubing will have a narrow bore diameter from 60 to 100 µm. In some embodiments, according to this aspect, the tubing will have a narrow bore diameter from 60 to 80 µm. In some embodiments, according to this aspect, the tubing will have a narrow bore diameter from 75 to 90 µm.

In some aspects, the tubing in the embodied infusion sets comprises at least a section having a narrow bore diameter of up to, at a maximum, 60 which in some embodiments, promotes or provides for pressurization of the primary container in the pump, which as a flexible container, needs some pressurization to maintain its shape and delivery accuracy during operation. In some embodiments, the tubing will have a narrow bore diameter from 20 to 60 µm.

In some embodiments, the narrow bore provides a flow restriction which damps out flow fluctuations and reduces siphoning effects.

Figure 4:
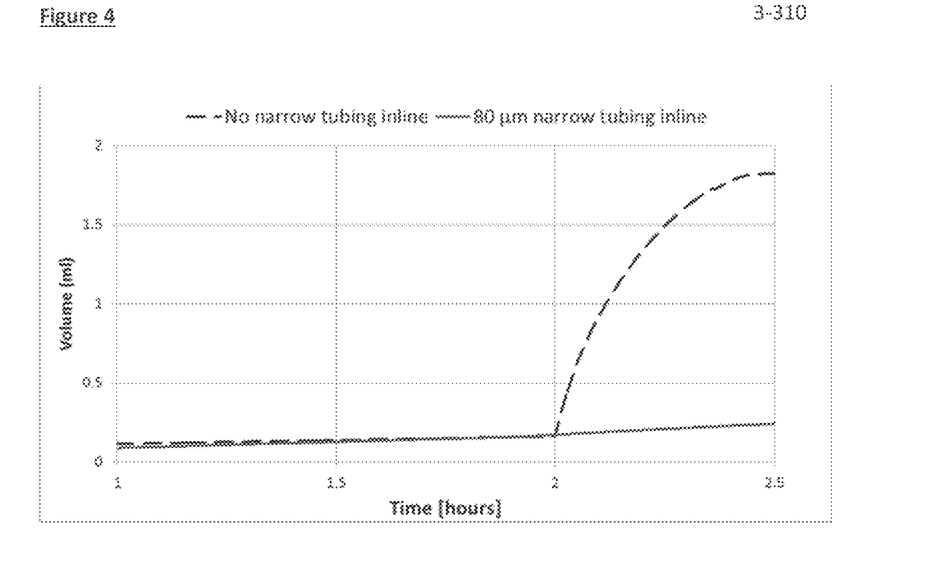
FIG. 4 plots the volume delivered by the pump through an embodied infusion set, as a function of time, when the tubing in the fusion line is either of narrow or normal bore. After 2 hours, an outlet of the tubing is raised by 30 cm relative to the pump, a siphoning effect is produced, which volume displacement is then measured.

FIG. 4 plots the results of an experiment conducted using two pumps, where a first pump was connected to an infusion set containing a proximally connected section with fine bore tubing, i.e. having an inner diameter of 80 microns and a second pump connected to a standard infusion set, having an inner bore diameter of 300 microns. Flow through each infusion set was measured by weighing the liquid exiting the tubing into respective collecting vessels, with the aid of an analytical scale. After two hours the pumps were elevated by 30 cm above the collecting vessel, generating artificial siphoning.

When assessing flow through an infusion set with fine bore tubing, the created siphoning effect on flow rate had a minor impact, in marked contrast to flow through the infusion set without a fine bore, which instead demonstrated significantly increased flow.

FIG. 4 supports the role for fine bore tubing preventing unwanted injection due to pump siphoning, in that after two hours lifting the two pumps 30 cm above the analytical scales level, showed dramatically different effects on the flow, and only the pump connected to an infusion set with fine bore tubing (solid line) showed stable flow, while the pump with standard tubing caused unwanted fluid to be expelled to the scales [Test setup was according to IEC 6061-2-24].

The following table presents the total volume measured 30 minutes following creation of the siphoning effect.

TABLE 1

|  | No Narrow tubing inline | 80 um narrow tubing inline |
|---|---|---|
| Siphoning bolus* (ml) | 1.6 | 0.03 |

Figure 5A:
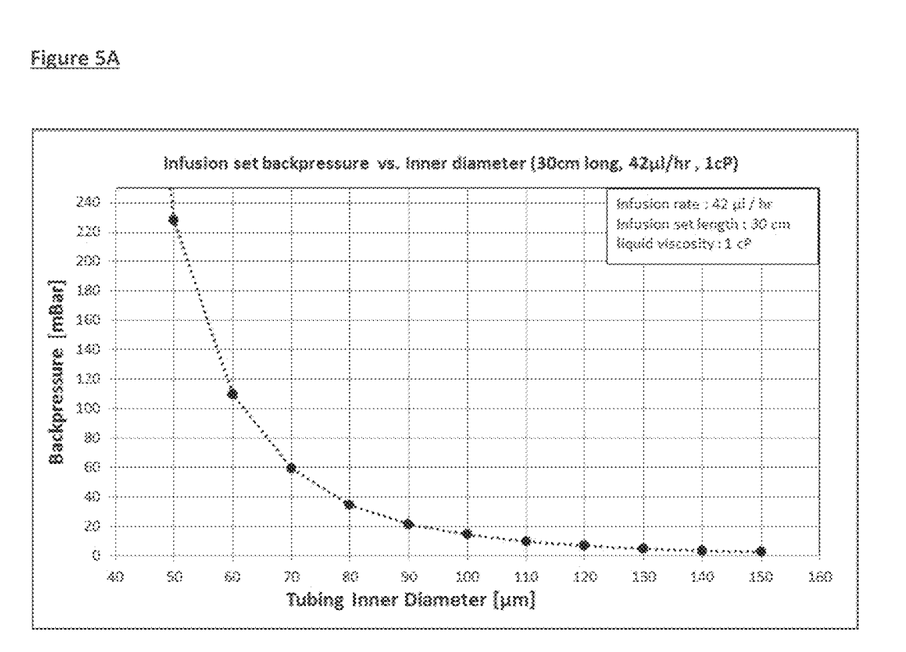
FIG. 5A plots theoretical backpressure as a function of tubing inner diameter or fluid viscosity, using a comparable experimental organization as depicted in FIG. 4.

Theoretical calculations were then derived, to demonstrate the dependency between inner diameter in the tubing of a putative infusion set and the backpressure created for a given flow, based on the Hagen-Poiseuille equation:

$$\Delta P = \frac{8 \ \mu L Q}{\pi r^4}$$

where
ΔP is the pressure loss
L is the length of pipe
μ is the dynamic viscosity
Q is the volumetric flow rate
r is the radius
d is the diameter
π is the mathematical constant Pi FIG. 5 plots the theoretical backpressure generated with different types of fine bore tubing sizes, where the controlled parameters are flow rate, infusion set length and liquid viscosity which are constant. The graph shows that for a constant flow rate, a smaller inner diameter in the tubing generates a higher pressure inside the container. Correct: this is simply plotting ΔP vs r where the other parameters are known While FIG. 5 indicated that an ideal backpressure may be generated by manipulating the bore size of the tubing in the infusion sets contemplated herein, it was then of interest to apply same to arrive at a more ideal means to promote critical restriction for optimal pump performance, i.e. to prevent pump siphoning and occlusion. In order to achieve such desired restriction, the theoretical calculations indicated a desired inner diameter of less than 100 μm.

Infusion sets having an inner diameter of less than 100 microns poses a significant challenge.

Thus various tubing permutations were prepared and assessed, and evaluated by microscopy, in order to ensure that the ideal dimensions and performance was obtained.

Figure 6A:
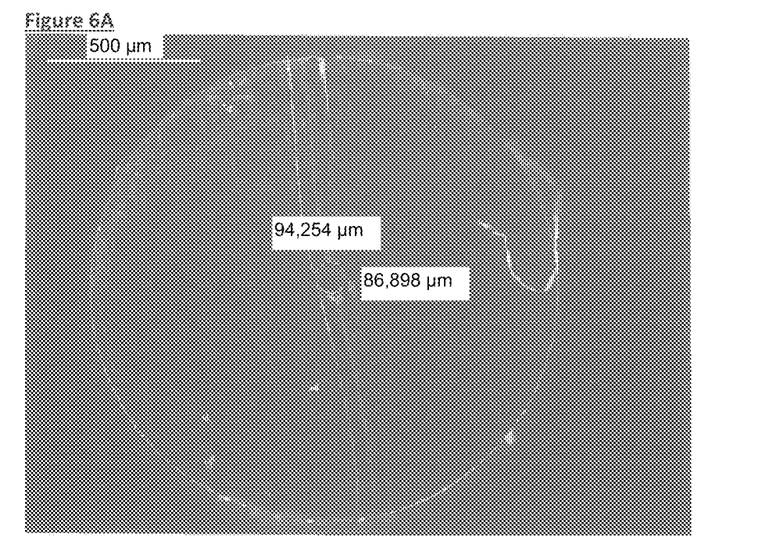
FIG. 6A is a micrograph showing the cross section of embodied fine bore tubing used in the infusion sets of this invention.

FIG. 6A presents a micrograph of embodied tubing for incorporation in the infusion sets as described herein, demonstrating the cross section of the fine bore tubing used in same. The photo demonstrates the dimensions of the inner bore and the average diameter measured was 90.9 μm.

Furthermore, it was of interest to verify that the cross section measurements were uniform through the entire tubing length and the impact of same on the restriction during pump operation.

Water was therefore injected through 30 cm tubing at different known pressures, and the flow through the opposite end of the tubing was then measured as described hereinabove, making use of analytical scales.

Figure 6B:
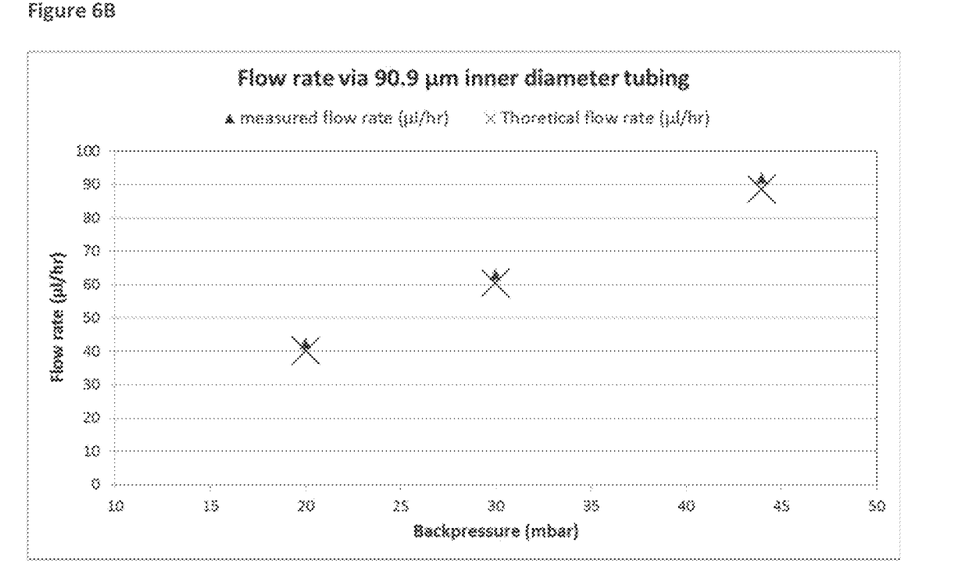
FIG. 6B plots the measured flow rates as compared to calculated flow rates for an embodied infusion set containing apparatus, when different backpressures were present when 90.9 micron tubing was used.

Since such parameters are known, the inner diameter/radius of the tubing can be calculated according to Hagen-Poiseuille equation: FIG. 6B plots the measured flow rates as compared to calculated flow rates for an embodied infusion set containing apparatus, when different backpressures were present when 90.9 micron tubing was used.

Table 2 presented below also presents the calculated versus obtained values of pressure differential required in order to facilitate mobilization of an air bubble through various sizes of narrow bore tubing.

TABLE 2

|  | Pressure [mBar] | Measured flow [μ/hr] | Calculated ID [μm] |
|---|---|---|---|
| Test #1 | 44 | 91.8 | 91.7 |
| Test #2 | 30 | 62.9 | 91.9 |
| Test #3 | 20 | 42.4 | 92.1 |
|  |  |  | Average - 91.9 |
|  |  |  | STD - 0.2 |

Figure 8:
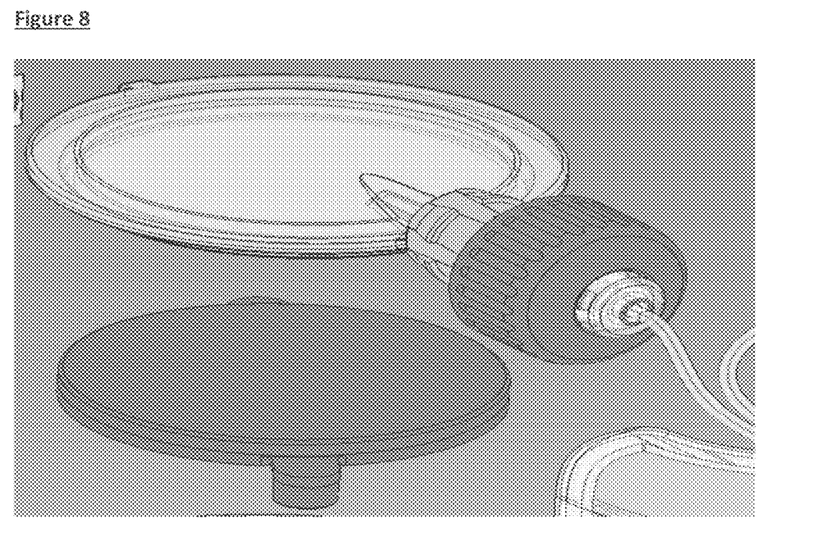
FIG. 8 schematically depicts connecting certain elements of an infusion set with elements of a patch pump delivery system.

FIG. 8 depicts an embodied infusion set containing key elements, which were prepared and an experimental setup making use of same is further exemplified below. A primary container, infusion set comprising a pump connector, needle, needle shroud and nut are depicted. Such an experimental embodied set was prepared with infusion set tubing of 30 cm in length, and containing a narrow bore diameter of 90 μm and the set was operationally connected to a piston, which pushes the liquid out from the primary container.

EXAMPLES

Example 1

Construction of an Embodied Infusion Set of this Invention

An experimental device setup was created to simulate key elements of an infusion set, containing an air bubble inside the drug reservoir container in the infusion pump. The desired outcome was that the air bubble located inside the container will not generate an occlusion in the tubing line.

The fluid path includes a primary container with infusion set connected. The bubble was pushed inside from the container and the pressure was monitored with a pressure meter. The elements are shown in FIG. 7, and approximate elements depicted in FIG. 8.

Using the designed elements of the experimental arrangement in FIG. 7, it was possible to measure the pressure necessary to mobilize an air bubble through the fine bore tubing of the experimental infusion set, and comparatively assess same versus theoretical calculations. Example 2 describes the obtained, measured results, whereas the theoretical calculations derived indicated that in order to mobilize an air bubble through 90 μm narrow bore tubing, an applied pressure of 32 mBar is required.

Example 2

The Embodied Infusion Sets of this Invention are Tolerant of Air Bubbles and Avoid Occlusion For an infusion set and infusion pump similar to that as described in FIG. 8 and as also described hereinabove, it was of interest to determine what theoretical pressure and what actual pressure would be required to remove an air bubble occluding an infusion line, and to assess whether the embodied infusion sets and apparatuses can readily address same.

Figure 7A:
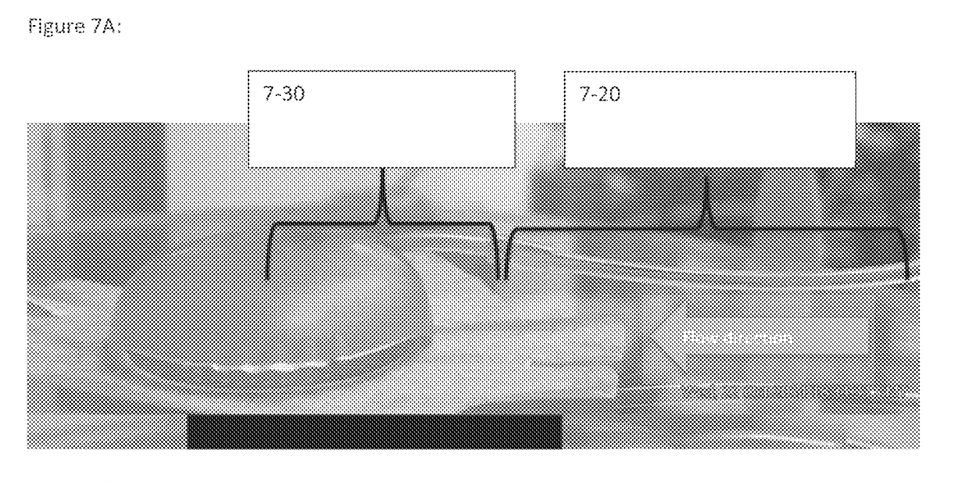
FIG. 7A is a photograph of an experimental protocol making use of embodied elements of embodied infusion sets of this invention.

Referring now to FIG. 7A, it is noted that a distal part of fine bore tubing (7-20) was connected to standard tubing (7-30) and the tubing was then extended to interface with a collection vessel and analytical scales arrangement as described herein.

Using the experimental setup depicted in FIG. 7A, an air bubble was deliberately introduced into the primary container and an increasing pressure was applied inside the primary container using a piston.

In the experimental setup depicted in FIG. 7A, 7-20 microbore tubing having a length of 30 cm and an inner diameter of 90.9 µm is connected to standard tubing 7-30 having a length of 2 cm and an inner diameter of 360 µm.

It is possible to arrive at a theoretical calculation of what pressure value should be applied to the system in order to move an air bubble trapped within the micro-bore tubing and preventing fluid flow into the standard tubing, to facilitate its release therefore and promote free fluid flow.

In a sufficiently narrow (i.e. low Bond number) tube of circular cross-section (radius a), the interface between the two fluids forms a meniscus that is a portion of the surface of a sphere within a radius R. The pressure jump across this surface is:

$$\Delta p = \frac{2\gamma}{R}.$$

Figure 7B:
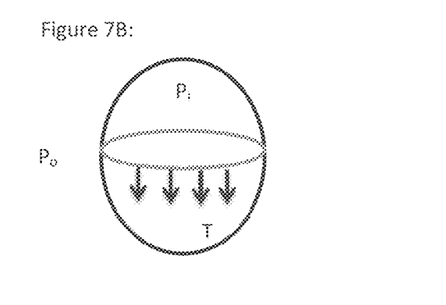
FIG. 7B schematically depicts the forces acting on a bubble in the system employed in FIG. 7A.

Referring now to FIG. 7B, the net upward force on the top hemisphere of a bubble (the air bubble) is the pressure difference times the area of the equatorial circle:

$$F_{upward} = (P_i - P_O)\pi R^2$$

The surface tension force downward around a circle is twice the surface tension times the circumference, since two surfaces contribute to the force:

$$F_{downward} = 2T(2\pi rR)$$

This yields:

$$P_i - P_0 = \frac{4T}{R} \text{ for a bubble}$$

$$P_i - P_0 = \frac{2T}{R} \text{ for a droplet which has only one surface}$$

The latter case also applies to the case of a bubble surrounded by a liquid, such as is evident in lung alveoli.

Applying this to the system described in FIG. 7A, yields a theoretical pressure required to push an air bubble through a 90.9 microns tubing of 32 mbar.

Micro-bore and standard tubing arranged as described in FIG. 7A filled with water for injection and operationally connected to the collection containers were prepared as described. An air bubble was introduced under low pressure within the tubing set, using the experimental setup as depicted.

As a result of introduction of the air bubble, the same transited a distance through the micro-bore tubing until it became stacked at the region closest to the joint region with the standard tubing.

Pressure was then manually applied to the flow path by pressing on the fluid filled container causing a burst of the air bubble in the micro-bore tubing, facilitating flushing of the air from the tubing into the colleting vessel placed on an analytical scale and located at the fluid path exit, and flow then resumed.

A pressure gauge connected thereto measured the internal pressure inside the primary container over the course of the entire experiment and the analytical scales measured the volume delivered to the containers.

The results showed that the air bubble occluded the infusion line during the first 1.2 hours until the pressure reached ~30-35. When the pressure was reached, the air bubble passed through the tubing line (1.2-1.5 hours) and the flow continued normally after 1.5 hours under constant pressure.

Figure 7C:
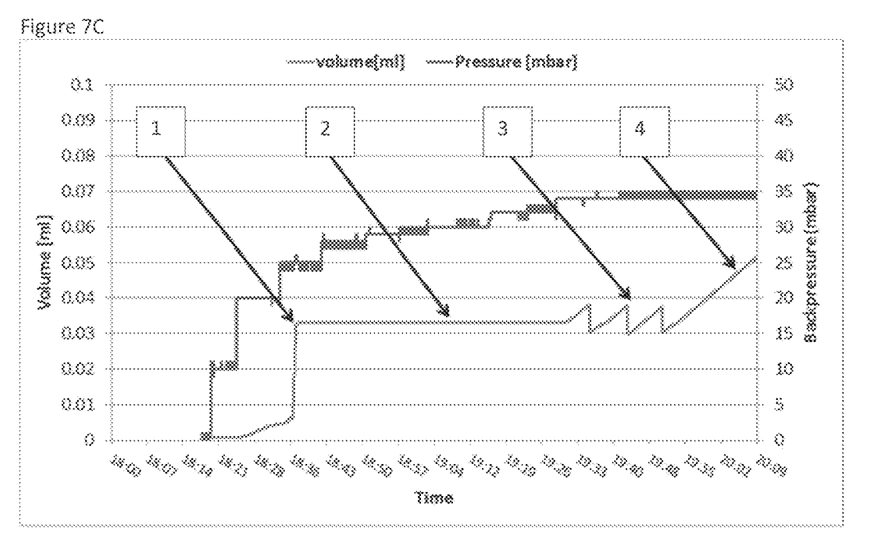
FIG. 7C plots the measured backpressure over time, in using the experimental system as described and depicted in FIG. 7A.

FIG. 7C plots the results of the experimental system as described above, conducted in order to arrive at the actual pressure required to push the air bubble through the micro-bore tubing in the system as described in FIG. 7A.

Points 1, 2, 3 and 4 describe the different stages encountered during the assay, and volume transit as a function of time in transit through the micro-bore tubing in the system.

Figure 7D:
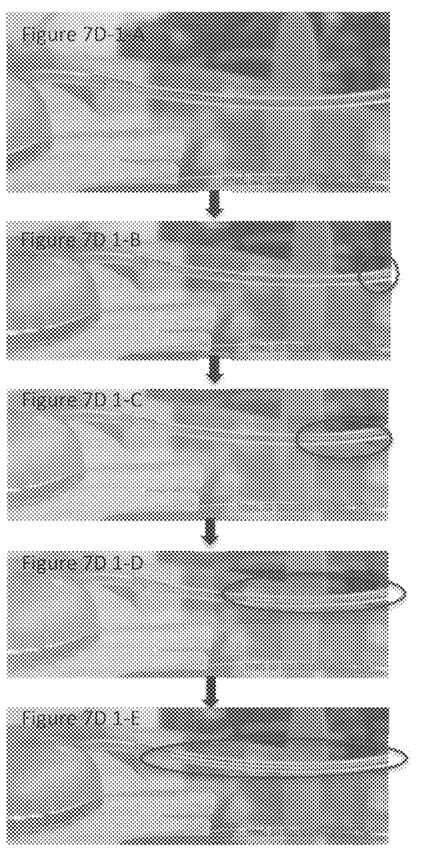
Figure 7E:
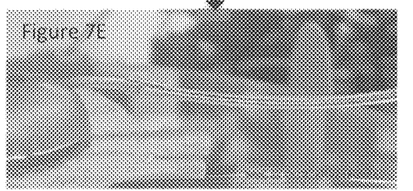
Figure 7F:
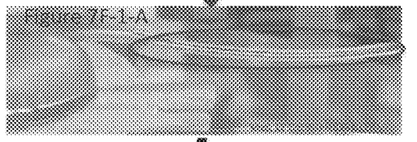

FIG. 7D describes the results which correspond to the values at point 1 of the graph in FIG. 7C. In this figure, after the tubing was filled with water for injection (1-A), an air bubble was injected at low pressure into the tubing set. The air bubble moved through the micro-bore tubing (1-B-1D) until it got stacked at the end of the tubing (1-E). The pressure applied during this stage was ~20-25 mbar FIG. 7E describes the results which correspond to the values at point 2 of the graph in FIG. 7C. In this figure, the air bubble became stuck inside the micro-bore tubing. The pressure applied during this stage was 15-35 mbar.

FIG. 7F describes the results which correspond to the values at point 3 of the graph in FIG. 7C. The pressure applied on the flow path reached the burst pressure of the air bubble which is flushed into the scales (1-A-1-F). The applied pressure was 35 mbar. Following this, the values at point 4 in the graph in FIG. 7C reflect flow returning to its normal rate, when the pressure applied is maintained at 35 mbar.

Thus, the actual pressure required was 35 mbar, similar to the calculated value of 32 mbar described above and there is remarkable agreement between the obtained and calculated values.

The ability to determine a burst pressure of the air bubble (32 mbar) extremely close in value to the nominal operation pressure of the pump (~20-30 mbar) indicated that the system is tolerant to occlusion caused by air bubbles and performs remarkably and unexpectedly well.

In general the term "comprise" or "comprising" also encompasses "consist of," "consist essentially of," "consisting of," or "consisting essentially of."

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications cited above is expressly incorporated herein by reference in their entireties to the same extent as if each were incorporated by reference individually.

What is claimed is:

1. A method of delivering medication, the method comprising:
   engaging a first connector comprising a lateral extension with an exit port of an infusion pump, wherein the engaging comprises:
   connecting a first terminus of a tubing to the exit port; wherein:

the tubing comprises a first tubing length having a bore with a first inner diameter from 40 microns to 150 microns, the tubing comprises a second tubing length having a second inner diameter, and the second inner diameter is larger than the first inner diameter;

actuating operation of the infusion pump to deliver fluid comprising medication from the infusion pump to the exit port by engaging the lateral extension with an actuator element of the infusion pump;

delivering the fluid through the tubing from the first terminus to a second terminus of the tubing, the second terminus connected by a second connector to a delivery module; and delivering the fluid from the tubing to the delivery module.

2. The method of claim 1, further comprising delivering the fluid to a patient subcutaneously or intravenously.

3. The method of claim 1, wherein engaging the first connector comprises fully engaging the first connector.

4. The method of claim 1, wherein actuating operation of the infusion pump does not require additional action from a user of the infusion pump.

5. The method of claim 4, further comprising operating, by the actuator element, a mechanical switch to initiate operation of the infusion pump.

6. The method of claim 4, further comprising operating, by the actuator element, a magnetic switch to initiate operation of the infusion pump.

7. The method of claim 1, further comprising preventing operation of the infusion pump when the first connector becomes fully or partially disconnected with the exit port.

8. The method of claim 1, wherein actuating operation of the infusion pump comprises magnetically actuating operation of the infusion pump.

* * * * *